United States Patent
Puntambekar et al.

(10) Patent No.: US 10,569,269 B2
(45) Date of Patent: Feb. 25, 2020

(54) METHODS FOR OPTIMIZING DETECTION OF IMMUNOASSAY REACTIONS CONDUCTED WITHIN A MICROFLUIDIC MICROPLATE

(71) Applicant: SILOAM BIOSCIENCES, INC., Forest Park, OH (US)

(72) Inventors: Aniruddha Puntambekar, Mason, OH (US); Se Hwan Lee, Camarillo, CA (US); Jungyoup Han, Cincinnati, OH (US); Chong H. Ahn, Cincinnati, OH (US); Winton Gibbons, San Diego, CA (US)

(73) Assignee: SILOAM BIOSCIENCES, INC., Seoul (KR)

( * ) Notice: Subject to any disclaimer, the term of this patent is extended or adjusted under 35 U.S.C. 154(b) by 236 days.

(21) Appl. No.: 15/866,636

(22) Filed: Jan. 10, 2018

(65) Prior Publication Data
US 2018/0141046 A1    May 24, 2018

Related U.S. Application Data

(63) Continuation-in-part of application No. 13/384,963, filed as application No. PCT/US2010/042506 on Jul. 20, 2010, now Pat. No. 9,919,311.
(Continued)

(51) Int. Cl.
*G01N 1/28* (2006.01)
*G01N 21/01* (2006.01)
(Continued)

(52) U.S. Cl.
CPC ....... *B01L 3/502715* (2013.01); *B01L 3/5025* (2013.01); *G01N 21/01* (2013.01);
(Continued)

(58) Field of Classification Search
CPC .......... B01L 2200/14; B01L 2300/069; B01L 2300/0829; B01L 2300/0858;
(Continued)

(56) References Cited

U.S. PATENT DOCUMENTS 6,322,683 B1    11/2001   Wolk et al.
6,485,690 B1 *  11/2002   Pfost ................... B01J 19/0046
                                                   422/552
(Continued)

*Primary Examiner* — Jennifer Wecker
(74) *Attorney, Agent, or Firm* — Dinsmore & Shohl LLP; Yongsok Choi, Esq.

(57) ABSTRACT

A method for reading a microfluidic microplate having a plurality of cells is provided. The method includes determining target locations on the microfluidic microplate, each of the target locations being deviated from a center of each of the cells, and directing a beam centered at each of the target locations perpendicular to the microfluidic microplate, the beam having a predetermined diameter. Each of the plurality of cells includes a well structure including a side wall for a loading well, a through hole at a center of a base of the well structure, and a microfluidic channel formed in a spiral pattern configured to start from a first end of the microfluidic channel and end with a second end of the microfluidic channel at the base of the well structure, wherein the first end of the microfluidic channel is connected to the through hole, and the second end of the microfluidic channel includes an outlet hole.

20 Claims, 12 Drawing Sheets

Related U.S. Application Data

(60) Provisional application No. 61/297,221, filed on Jan. 21, 2010, provisional application No. 61/226,764, filed on Jul. 20, 2009.

(51) Int. Cl.

| | | |
|---|---|---|
| *B01L 3/00* | (2006.01) | |
| *G01N 21/76* | (2006.01) | |
| *G01N 33/543* | (2006.01) | |
| *G01N 21/25* | (2006.01) | |
| *B01L 9/00* | (2006.01) | |
| *G01N 21/27* | (2006.01) | |

(52) U.S. Cl.
CPC ........... *G01N 21/253* (2013.01); *G01N 21/76* (2013.01); *G01N 33/54366* (2013.01); *B01L 9/523* (2013.01); *B01L 2200/14* (2013.01); *B01L 2300/069* (2013.01); *B01L 2300/088* (2013.01); *B01L 2300/0829* (2013.01); *B01L 2300/0858* (2013.01); *B01L 2300/0883* (2013.01); *B01L 2300/0893* (2013.01); *B01L 2400/0406* (2013.01); *B01L 2400/086* (2013.01); *G01N 21/272* (2013.01)

(58) Field of Classification Search
CPC ....... B01L 2300/088; B01L 2300/0883; B01L 2300/0893; B01L 2400/0406; B01L 2400/086; B01L 3/5025; B01L 3/502715; B01L 9/523; G01N 21/01; G01N 21/253; G01N 21/272; G01N 21/76; G01N 33/54366

See application file for complete search history.

(56) References Cited

U.S. PATENT DOCUMENTS

| | | |
|---|---|---|
| 2005/0266582 A1 | 12/2005 | Modlin et al. |
| 2007/0003448 A1* | 1/2007 | Kanigan ............... B01L 3/5025 422/400 |
| 2007/0014695 A1 | 1/2007 | Yue et al. |
| 2007/0166771 A1 | 7/2007 | Kapur et al. |
| 2008/0115599 A1 | 5/2008 | Masters et al. |
| 2009/0004754 A1 | 1/2009 | Oldenburg et al. |
| 2009/0136982 A1 | 5/2009 | Tang et al. |
| 2011/0124130 A1 | 5/2011 | Wagner et al. |

* cited by examiner

METHODS FOR OPTIMIZING DETECTION OF IMMUNOASSAY REACTIONS CONDUCTED WITHIN A MICROFLUIDIC MICROPLATE

CROSS-REFERENCE TO RELATED APPLICATION

This application is a continuation-in-part application of the U.S. patent application Ser. No. 13/384,963 filed on Aug. 31, 2012 which is a national stage application of International Patent Application No. PCT/US10/042506 filed on Jul. 20, 2010 which claims the benefits of U.S. Provisional Application No. 61/226,764 filed on Jul. 20, 2009 and U.S. Provisional Application No. 61/297,221 filed on Jan. 21, 2010.

FIELD

This invention relates to methods for optimizing the detection of immunoassay reactions conducted within a microfluidic microplate.

BACKGROUND

Immunoassay techniques are widely used for a variety of applications as described in "Quantitative Immunoassay: A Practical Guide for Assay Establishment, Troubleshooting and Clinical Applications; James Wu; AACC Press; 2000". The most common immunoassay techniques are 1) non-competitive assay: an example of such is the widely known sandwich immunoassay, wherein two binding agents are used to detect an analyte; and 2) competitive assay: wherein only one binding agent is required to detect an analyte.

In its most basic form, the sandwich immunoassay (assay) can be described as follows: a capture antibody, as a first binding agent, is coated (typically) on a solid-phase support. The capture antibody is selected such that it offers a specific affinity to the analyte and ideally does not react with any other analytes. Following this step, a solution containing the target analyte is introduced over this area whereby the target analyte conjugates with the capture antibody. After washing the excess analyte away, a second detection antibody, as a second binding agent, is added to this area. The detection antibody also offers a specific affinity to the analyte and ideally does not react with any other analytes. Furthermore, the detection antibody is typically "labeled" with a reporter agent. The reporter agent is intended to be detectable by one of many detection techniques such as optical (fluorescence or chemiluminescence or large-area imaging), electrical, magnetic or other means. In the assay sequence, the detection antibody further binds with the analyte-capture antibody complex. After removing the excess detection antibody; finally the reporter agent on the detection antibody is interrogated by means of a suitable technique. In this format, the signal from the reporter agent is proportional to the concentration of the analyte within the sample. In the so called "competitive" assay, a competing reaction between detection antibody and (detection antibody+analyte) conjugate is caused. The analyte, or analyte analogue is directly coated on the solid phase and the amount of detection antibody linking to the solid-phase analyte (or analogue) is proportional to the relative concentrations of the detection antibody and the free analyte in solution.

SUMMARY

In one embodiment, a method for reading a microfluidic microplate having a plurality of cells is provided. The method includes determining target locations on the microfluidic microplate, each of the target locations being deviated from a center of each of the cells, and directing a beam centered at each of the target locations perpendicular to the microfluidic microplate, the beam having a predetermined diameter. Each of the plurality of cells includes a well structure including a side wall for a loading well, a through hole at a center of a base of the well structure, and a microfluidic channel formed in a spiral pattern configured to start from a first end of the microfluidic channel and end with a second end of the microfluidic channel at the base of the well structure, wherein the first end of the microfluidic channel is connected to the through hole, and the second end of the microfluidic channel includes an outlet hole.

In another embodiment, a method for reading a microfluidic microplate having a plurality of cells is provided. The method includes determining a plurality of reading locations for each of the plurality of cells, each of the reading locations being deviated from a center of each of the plurality of cells; and directing a beam centered at each of the plurality of reading locations perpendicular to the microfluidic microplate, the beam having a predetermined diameter. Each of the plurality of cells includes a well structure including a side wall for a loading well, a through hole at a center of a base of the well structure, and a microfluidic channel formed in a spiral pattern configured to start from a first end of the microfluidic channel and end with a second end of the microfluidic channel at the base of the well structure. The first end of the microfluidic channel is connected to the through hole, and the second end of the microfluidic channel includes an outlet hole.

In another embodiment, a method for reading a microfluidic microplate having a plurality of cells is provided. The method includes directing a beam at each of the plurality of cells perpendicular to the microfluidic microplate, obtaining assay signals for each of the plurality of cells, and compensating the assay signals based on timings of reading the plurality of cells. Each of the plurality of cells includes a well structure including a side wall for a loading well, a through hole at a center of a base of the well structure, and a microfluidic channel formed in a spiral pattern configured to start from a first end of the microfluidic channel and end with a second end of the microfluidic channel at the base of the well structure. The first end of the microfluidic channel is connected to the through hole, and the second end of the microfluidic channel includes an outlet hole.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

As referenced herein, μF96 or μf96, or the Optimiser™, refer to a 96 well microfluidic microplate wherein each well is connected to at least one microfluidic channel. Unless otherwise explicitly described, the microfluidic microplate shall be assumed to be made of 3 functional layers, namely the substrate layer (with the wells, through-hole structures and microfluidic channels), the sealing tape layer, and an absorbent pad layer; wherein the "96" refers to a 96 well layout and similarly μf384 would refer to a 384 well layout and so forth. The term Optimiser™ is also used to describe the present microfluidic microplate and similarly, Optimiser™-96 shall refer to a 96 well layout, Optimiser™-384 shall refer to a 384 well layout and so forth. Furthermore, "microfluidic channel" and "microfluidic channel" and "channel" all refer to the same fluidic structure unless otherwise dictated by the context. The term "interface hole" or "through hole" or "via hole" all refer to the same structure connecting the well structure to the microfluidic channel structure unless dictated otherwise by the context. The term "cell" is used to describe a functional unit of the microfluidic microplate wherein the microfluidic microplate contains multiple essentially identically "cells" to comprise the entire microplate.

Figure 1:
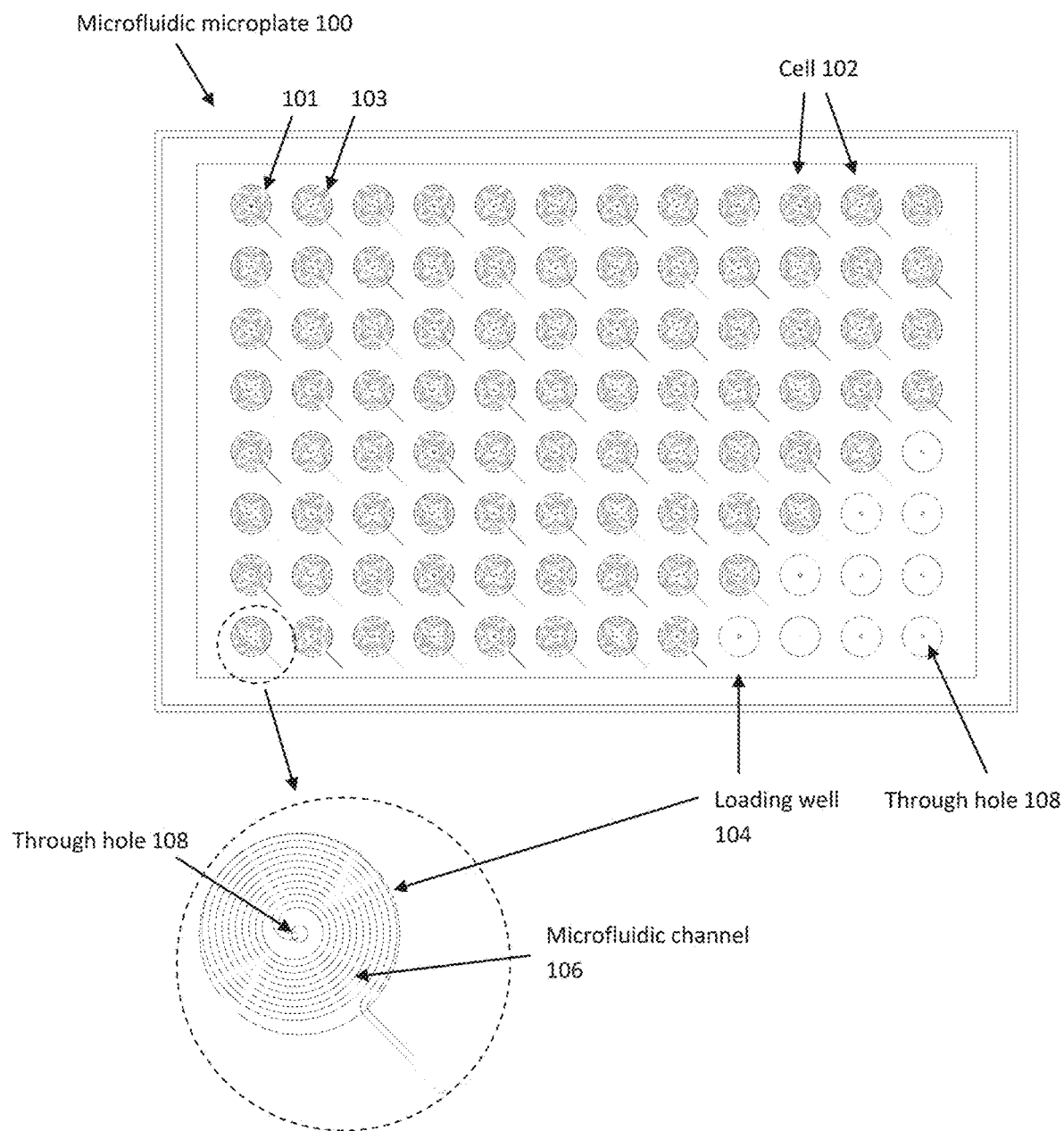
FIG. 1 depicts a top view of a microfluidic microplate according to one or more embodiments shown and described herein.

FIG. 1 shows the top of view of the microfluidic microplate 100 (e.g., microfluidic 96 well plate). The microfluidic microplate 100 may include 96 cells 102. Each of the cells 102 includes a loading well 104. The microfluidic microplate 100 may match the dimensions of conventional microplates (as defined by accepted ANSI standards). The positions of the loading wells 104 also may match ANSI standards. Each of the loading wells 104 includes a through hole 108 at its center. The through hole 108 is connected to a microfluidic channel 106 on the opposing face of the microfluidic microplate 100. FIG. 1 does not show a sealing layer (for microfluidic channels) and an absorbent pad for clarity. Also, selected wells in lower right hand corner of FIG. 1 do not show microfluidic channel pattern for ease of explanation. In the embodiment shown in FIG. 1, the loading wells 104 and the microfluidic channels 106 are fabricated on the same substrate layer. A noteworthy feature of the present disclosure is understood from FIG. 1. The loading position (for adding liquid reagents) and the detection region are in the same vertical plane; which matches the conventional microplate exactly.

Figure 2:
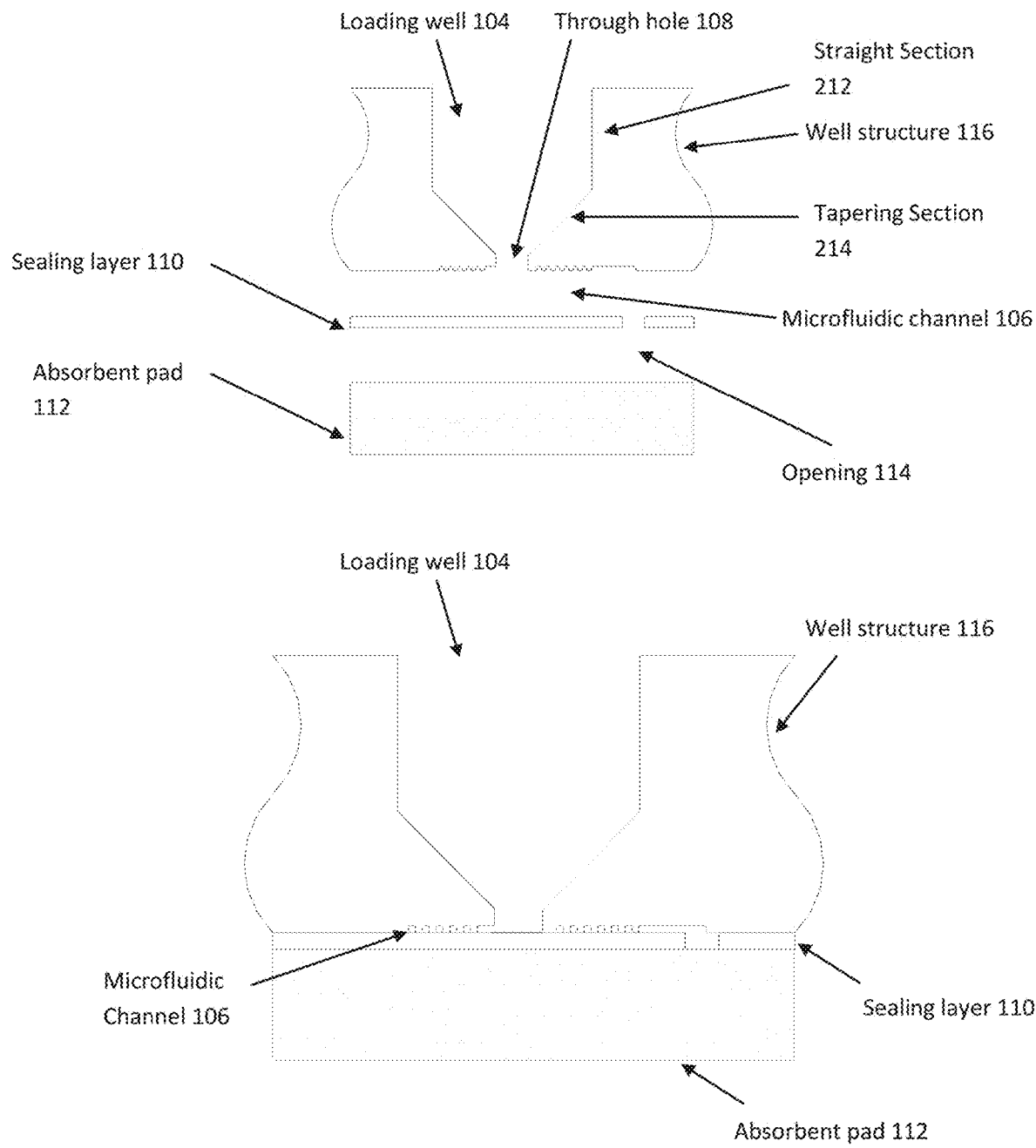
FIG. 2 depicts a cross sectional view of a cell of the microfluidic microplate according to one or more embodiments shown and described herein.

FIG. 2 shows cross-sectional views of a portion of the microplate showing 1 unit of 96 in exploded and assembled views. Each loading well 104 is connected to the microfluidic channel 106 on the opposing face of the microfluidic microplate 100. Microfluidic channels 106 are sealed by a sealing layer 110 (e.g., a tape) which in turn has an opening 114. The opening 114 on the sealing layer 110 connects one end of the microfluidic channel 106 to an absorbent pad 112. When liquid is introduced in the well, it is drawn into the microfluidic channels 106 by capillary force. The liquid travels along the microfluidic channel 106 until it reaches the opening in the sealing layer 110. Thereupon, liquid front contacts the absorbent pad 112 which exerts stronger capillary force and draws liquid until the loading well 104 is emptied. Depending on the interface configuration at well-microfluidic channel interface, the liquid will also be emptied from the microfluidic channel 106 or liquid motion will stop when rear end of liquid column reaches well-microfluidic channel interface. In latter case, the liquid is still filled in the microfluidic channel 106.

Figure 3:
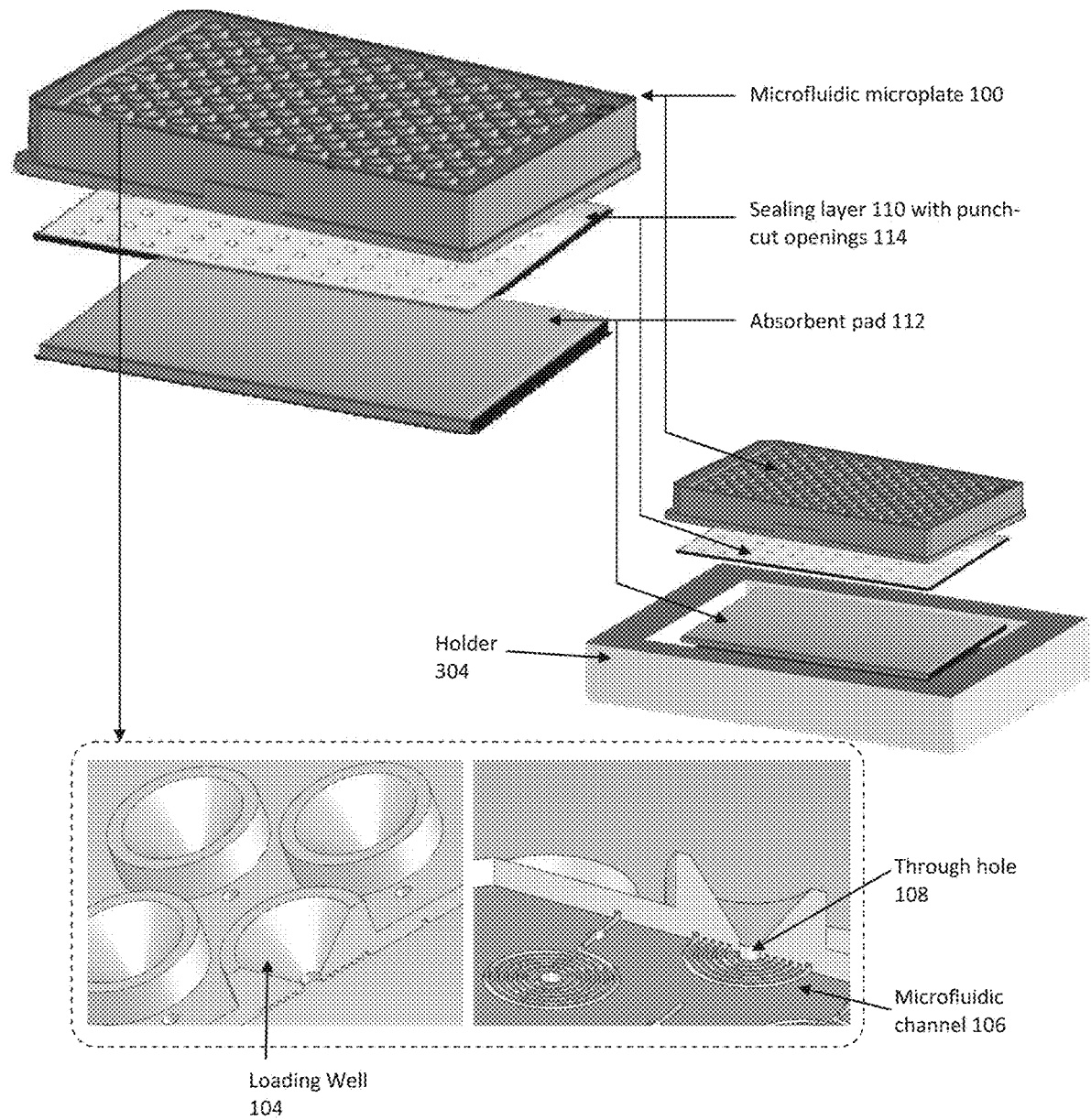
FIG. 3 depicts a three-dimensional illustration of a microfluidic microplate according to one or more embodiments shown and described herein.

FIG. 3 shows 3-dimensional view of the microfluidic microplate 100, the sealing layer 110, and the absorbent pad 112 in exploded view, and 3-dimensional view of the microfluidic microplate 100, the sealing layer 110, and the absorbent pad 112, and a holder 304 in exploded view. Each loading well 104 is connected to the corresponding microfluidic channel 106 on the opposing face of the microfluidic microplate 100. Microfluidic channels 106 are sealed by the sealing layer 110 which in turn has an opening 114 at the other end of the microfluidic channel (as compared to the end connected to the through hole 108 at the bottom of the loading well 104). The opening 114 on the sealing layer 110 connects on the other side to the absorbent pad 112. In the preferred embodiments, an array of absorbent pads 112 are used such that the absorbent pads 112 are not in the same vertical line of sight as the loading well 104 and the microfluidic channels 106. Alternately, as shown in FIG. 3, the absorbent pad 112 can be a single continuous piece connected to all the 96 microfluidic channel outlets. When liquid is introduced in the loading well 104, it is drawn into the microfluidic channels 106 by capillary force; the liquid travels along the microfluidic channel 106 until it reaches the opening 114 in the sealing layer 110. Thereupon, liquid front contacts the absorbent pad 112 which exerts stronger capillary force and draws liquid until well is emptied. In embodiments, the through hole 108, the microfluidic channels 106 and the absorbent pad 112 are configured such that as the liquid exits the loading well 104 the rear end of the liquid column cannot move past the interface between the through hole 108 and the microfluidic channel 106. Consequently, the loading well 104 is completely emptied of its liquid contents and the liquid is partially absorbed by the absorbent pad 112 whereas a portion of the liquid still occupies the complete microfluidic channel 106. This configuration can be used as an incubation step for immunoassay based analysis.

When a second liquid is added to the well, the second liquid makes contact with the rear end of the first liquid at the interface of the through hole 108 and the microfluidic channel 106. At this stage, there is again a continuous liquid column from the absorbent pad extending via the microfluidic channel 106 and the through hole 108 to the loading well 104. The lower surface tension of the liquid column filling the loading well 104 will cause flow to resume and the first liquid will be completely drawn out of the microfluidic channel 106 and replaced by the second liquid. The second liquid will also be drawn out of the microfluidic channel 106 until the rear end of the second liquid now reaches the interface between the through hole 108 and the microfluidic channel 106 where the flow will stop again. This sequence is continued until all steps required for an immunoassay are completed. This also illustrates a particularly advantageous aspect of the present disclosure—namely the fact that the sequence of operation only involves liquid addition steps. There is no need to remove the liquid from the well since it is automatically drained out. This considerably reduces the number of steps required for operation and simplifies the operation of the microfluidic microplate. Also, as described earlier, in embodiments, the absorbent pads 112 are positioned such that the absorbent pads 112 are not in the same vertical line of sight as the reaction chambers. In this scheme the absorbent pads 112 can be integral to the microfluidic microplate 100; whereas if desired, the absorbent pads 112 can be configured to a removable component that can be discarded after the last liquid loading step, for example in the case of the embodiment shown in FIG. 3.

In embodiments, the microfluidic microplate 100 containing the loading wells 104, the through holes 108 and the microfluidic channels 106 may be transparent. This allows for optical monitoring of the signal from the microfluidic channel from the top as well as bottom of the microplate; a feature that is common on a wide variety of microplate readers used in the art. In other embodiments, the microfluidic microplate 100 may be an opaque material such that the optical signal from the microfluidic channel 106 may only be read from the face containing the microfluidic channel. For example, in the embodiment shown in FIG. 2, the signal may only be read from the "bottom" if the microfluidic microplate 100 were an opaque material. As described later, yet another method may use rotation of an insert layer to allow for top reading with an opaque substrate material.

The microfluidic microplate 100 can be manufactured by a conventional injection molding process and all commonly used thermoplastics suitable for injection molding may be used as a substrate material for the microfluidic microplate. In embodiments, the microfluidic microplate 100 is made from a Polystyrene material which is well known in the art as a suitable material for microplates. In other embodiments, the microfluidic microplate 100 is made from Cyclic Olefin Copolymer (COC) or Cyclic Olefin Polymer (COP) materials which are known in the art to exhibit a lower autofluorescence and consequently lower background noise in fluorescence or absorbance based detection applications.

An example assay sequence for a sandwich immunoassay is described next. By using well known techniques in the art; a wide variety of such assays can be performed on the microfluidic microplate 100. As is readily evident from the description; all of the reagent addition steps can be performed by automation systems designed to handle liquids for current microplate formats without any changes.

In embodiments, the following sequence may occur:
1. To cause a flow sequence; the first liquid is pipetted into the well.
2. The volume of the liquid loaded into the well should be at least slightly larger than the internal volume of the channel.
3. The liquid will be drawn into the microfluidic channel and will continue to move due to capillary force.
4. The liquid will flow from the well via the channel till it reaches the outlet where it will touch the absorbent pad.
5. After this, the absorbent pad will continue to draw the liquid till all the liquid in the well is emptied into the channel and then into the pad. The liquid flow will stop when the rear end of the liquid column reaches the interface between the through hole at the base of the well and the channel.
6. The flow rate in this configuration is completely controlled by (a) liquid type; (b) geometries of well and channel and interface ports (namely the through hole) (c) material properties of the microfluidic (or Optimiser™) microplate; specifically surface properties; and (d) absorbing characteristic of the pad.
   a. The flow rate can be manipulated by varying any one of the parameters.
   b. The initial "filling" flow rate is independent of the pad and is based only on channel properties
   c. Thereafter the channel acts as a fixed resistance (except at the very end when the liquid is emptying) and the pad acts as a vacuum (or capillary suction) source.
   d. If desired, the assay steps can be under static incubation to ensure that there is minimal effect of flow rate variation on assay response.
7. After this a second liquid may be added and the same sequence can be repeated.
   a. Alternately, the second liquid can be loaded just as the first liquid is emptying from the well. This will lead to a continuous liquid column without a stop in flow between the first and second liquid.
8. After the last liquid that should be added is passed through the system, the absorbent pad(s) may be removed if desired. The lack of further capillary force will guarantee a stop to the liquid motion.
9. The plate can be read from the top of the well or from the bottom side or if the well structure interferes with optical signals, the μf96 (or Optimiser™) may be flipped over and read from the channel side. If the latter is required, the plate configuration should be modified such that the plate still fits a standard holder for SBS/ANSI 96 well plates.

Resulting assay, example:
1. Add capture antibody and flow—capture antibody will non-specifically adsorb on channel surface. Repeated injections of capture antibody solution can potentially increase concentration on surface.
2. Wait till the capture antibody solution is completely sucked through the well. The capture antibody solution is still completely filling the microfluidic channel. Incubate to allow capture antibody conjugation to channel surface.
3. Add blocking buffer and flow; incubate to allow blocking media to conjugate to remaining channel surface.
4. Add sample and flow; incubate to allow target analyte to link with capture antibody
   a. Optionally, repeated injections of sample can increase detection sensitivity
5. (Optional) flush again
6. Add labeled detection antibody and flow; incubate to allow detection antibody to conjugate to captured target analyte
7. Flush with buffer 8. For Fluorescence based assay, the plate can now be transferred to reader 9. For luminescence of chemifluorescence assay—add substrate which will fill channel and allow it to incubate 10. For luminescence or chemifluorescence assay, the plate can now be transferred to reader The well structure shown in FIG. 2 comprises a straight (cylindrical) section 212 and a tapering (conical) section 214. The tapering section 214 allows for complete flushing out of well contents as opposed to having a small through hall at the base of a cylindrical well structure. It will be appreciated that a wide variety of configurations are possible for this basic scheme; for instance when the through hole 108 may not be at the center of the loading well 104 but offset to one side; or wherein the microfluidic channel pattern is of different configuration; or wherein the absorbent pad may be placed in a different position; or wherein the relative depth and/or position of the well structure and microfluidic channel with respect to total plate thickness (set as 14.35 mm by SBS/ANSI standards) is varied. Indeed, although highly desirable for standardization, the microfluidic microplate 100 may also be made to dimensions not confirming to the ANSI/SBS specs in certain examples. A few of these are described as examples of embodiments possible with this concept. The embodiments described herein are merely to illustrate the flexibility of this concept and are not intended to limit the present invention.

One embodiment is shown in the 3-dimensional (3D) view of FIG. 3. As shown in FIG. 3, the loading well 104 does not have a straight section at the top, but only a taper section. This minimizes the potential for any residue at the transition point from the vertical wall to the tapered wall of the well. Also, as shown in FIG. 2 and FIG. 3, the loading well 104 may be configured such that the microfluidic microplate 100 completely surrounds the well or the surrounding substrate may be created in the form of "lip" structure. The latter minimizes the amount of polymer material required for the part thereby reducing cost. The use of the "lip" structure also makes the part more amenable to injection molding operations since the lower amount of material in this configuration exhibits less shrink during the molding process; which is advantageous since said shrink may cause distortion of the well, through hole and microfluidic channel patterns.

Figure 4A:
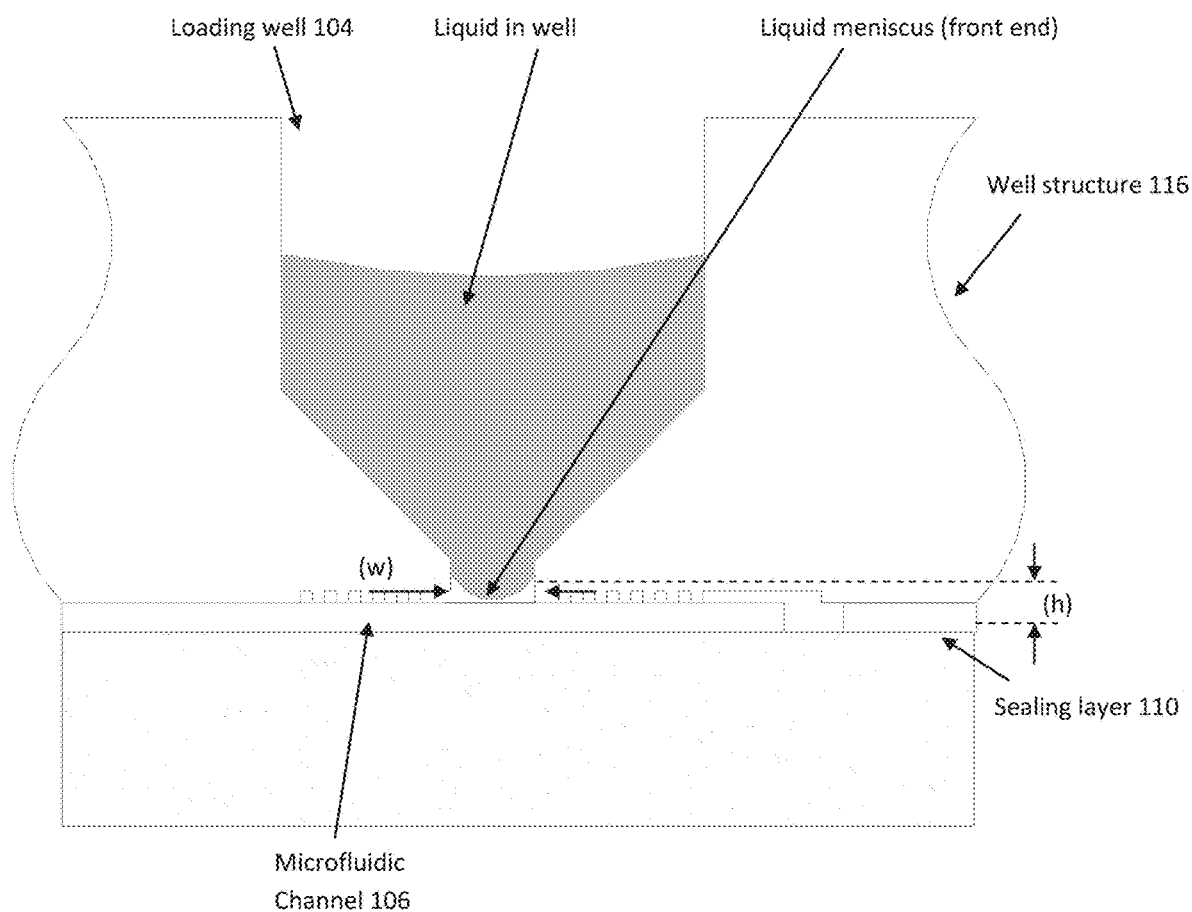
FIG. 4A depicts a cross sectional view of a cell of the microfluidic microplate according to one or more embodiments shown and described herein.

Another embodiment is shown in FIG. 4A. As shown in FIG. 4A, the width of the through hole (w) may be greater than, and at least equal to, the depth (d) of the through hole 108. This ensures that when liquid is introduced in the loading well 104, the front meniscus of the liquid can "dip" and touch the surface of the sealing layer 110. The meniscus also touches all 4 "walls" of the microfluidic channel 106 connected to one part of the through hole 108 (left hand side in above referenced figure). Thereafter, capillary forces will draw the liquid from the well and fill the microfluidic channel 106. In order to ensure that the liquid fills the microfluidic channel 106 at least one of the walls of the microfluidic channel should be hydrophilic. In an embodiment, the sealing layer 110 is an appropriate adhesive film wherein the adhesive exhibits a hydrophilic behavior. This will ensure that when the liquid is loaded into the loading well 104 and the front meniscus touches the sealing layer 110, the liquid will "spread" on the sealing layer 110; touch the microfluidic channel 106 and thereafter continue to be drawn into the microfluidic channel 106. In alternate embodiments, the sealing layer 110 may be another plastic that is similar to the one used to fabricate the well and channel structures and the two are assembled using techniques well known in the art such as thermal bonding, adhesive film assisted bonding, laser or ultrasonic bonding to name a few. In the alternate embodiment; the microfluidic channel 106 may be "primed" by forcing a first liquid through the microfluidic channel 106. This can be easily accomplished by positioning a pipette tip or other suitable liquid handling tool against the interface hole such that it creates a reasonable seal. Then, injection of liquid will result in at least a part of the liquid being injected in the channel and thereafter capillary forces will ensure that the liquid continues to fill the channel.

In some embodiments, not just the initial but all assay steps can also be easily performed by injecting solutions directly in the microfluidic channels and wherein the well structure is only used a guide for the pipette or other fluid loading tool. In yet another embodiment, all the walls of the microfluidic channel are treated to be hydrophilic by appropriate choice of surface treatments that are well known in the art. In yet another embodiment, the substrate material including all microfluidic channel walls can be rendered hydrophilic using techniques well known in the art; and a hydrophobic sealing tape may be used. The choice of surface treatment (i.e. final surface tension of the walls with respect to liquids) depends on the intended assay application. In most cases, it is preferred to have a hydrophobic surface to allow for hydrophobic interaction based binding of biomolecules to the surface. In other cases, a hydrophilic surface may be more suitable for hydrophilic interactions of the biomolecule with the binding surface; and in even other cases; a combination of hydrophobic and hydrophilic surface may be desired to allow both types of biomolecules to bind.

In yet another embodiment, a first "priming" liquid is used to fill the microfluidic channel. Liquids such as Isopropyl Alcohol exhibit an extremely low contact angle with most polymers and exhibit very good wicking flow. Such a liquid will fill the channel regardless of whether the microfluidic channel walls are hydrophilic or hydrophilic. Once the liquid contacts the absorbent pad a continuous path is created to the loading well. Liquids added thereafter will be automatically drawn into the microfluidic channel. In combination with the microfluidic channel surface, the well surface may also be modified to enhance or detract from the capillary forces exerted on the liquid column. For example, if a strongly hydrophilic treatment is rendered on the well surface, the rear meniscus will have a strongly concave shape wherein the bulge of the meniscus is directed towards the bottom of the well. This meniscus shape will compete with the meniscus shape at the front end of the liquid column (before it touches absorbent pad) and ensure a slow fill. If on the other hand the well surface is rendered strongly hydrophobic the rear meniscus may achieve a convex shape wherein the bulge of the meniscus is towards the top of the well. This meniscus shape will add to the capillary force present at the front end of the liquid column and cause a faster flow rate.

Figure 4B:
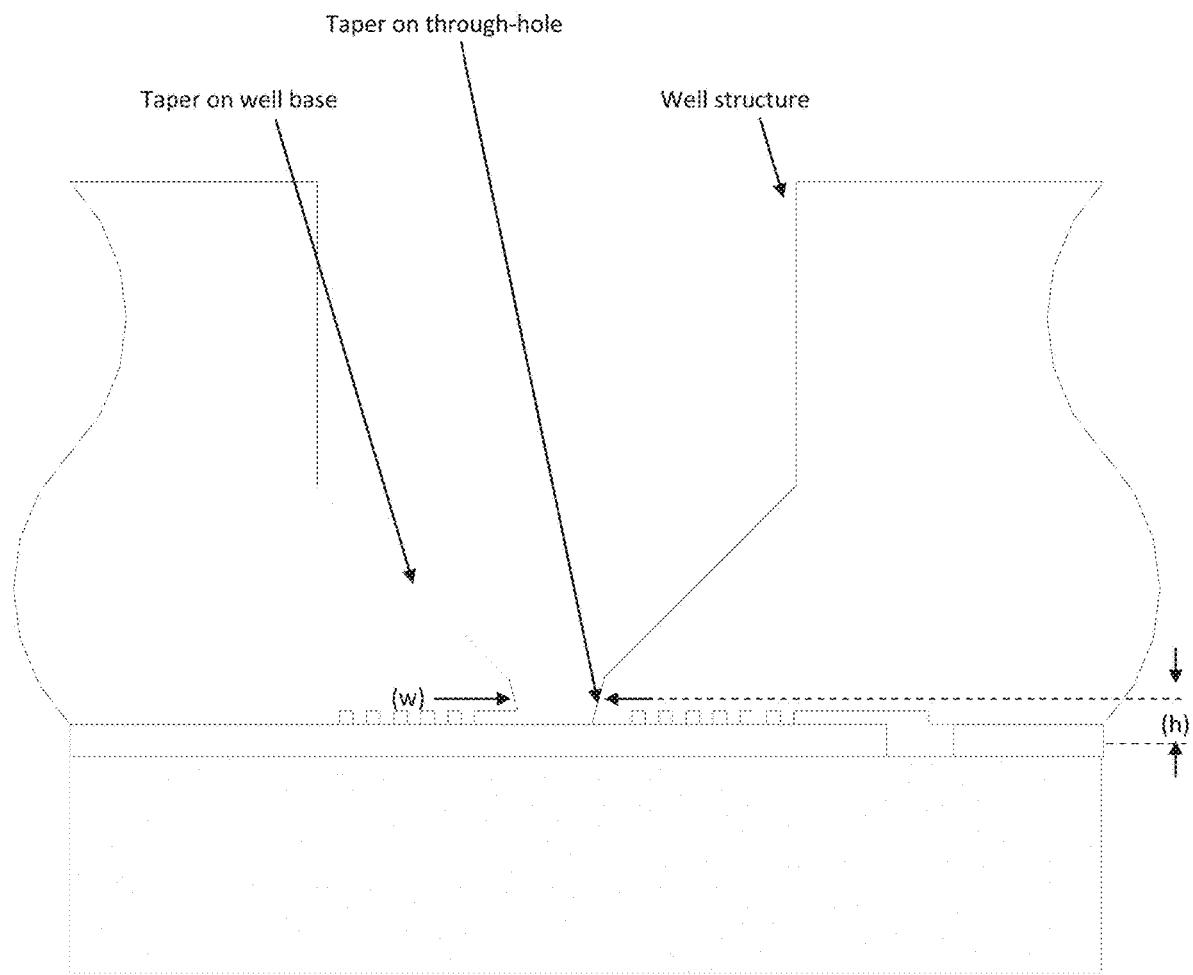
FIG. 4B depicts a cross sectional view of a cell of the microfluidic microplate according to another embodiment shown and described herein.

In another embodiment shown in FIG. 4B, the through-hole structure itself may be tapered rather than a cylindrical geometry with straight sidewalls as shown in FIG. 4A. In FIG. 4B, the width of the through hole at the top (w) shall be greater than, and at least equal to, the depth (d) of the hole; and furthermore the through-hole shall also have tapered walls. The taper angle (with respect to horizontal) of the walls of the through hole will be greater than or equal to the taper angle on the walls at the base of the well structure immediately preceding the through hole. This ensures that when liquid is introduced in the well, the front meniscus of the liquid can "dip" and touch the surface of the sealing tape. The meniscus also touches all 4 "walls" of the microchannel connected to one part of the hole (left hand side in above figure). Thereafter, capillary forces will draw the liquid from the well and fill the microchannel.

In yet other embodiments; the well and through-hole structures shown in FIG. 4A or FIG. 4B may be selectively treated to impart a different surface functionality. For instance, the substrate layer may be substantially hydrophobic with only the inside surface of well and the through-hole treated to be hydrophilic. The substrate layer is turn sealed by a hydrophilic tape. Hence in this configuration; there is a continuous hydrophilic path from the well to the through hole to the base of the microfluidic channel (tape) ensuring that the liquid consistently fills the microfluidic channel without any intervening air bubbles.

Figure 5A:
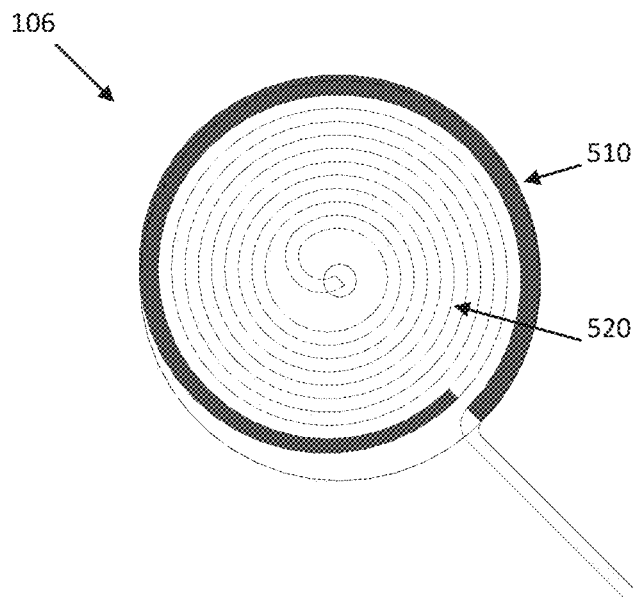
FIG. 5A depicts a microfluidic channel according to one or more embodiments shown and described herein.
Figure 5B:
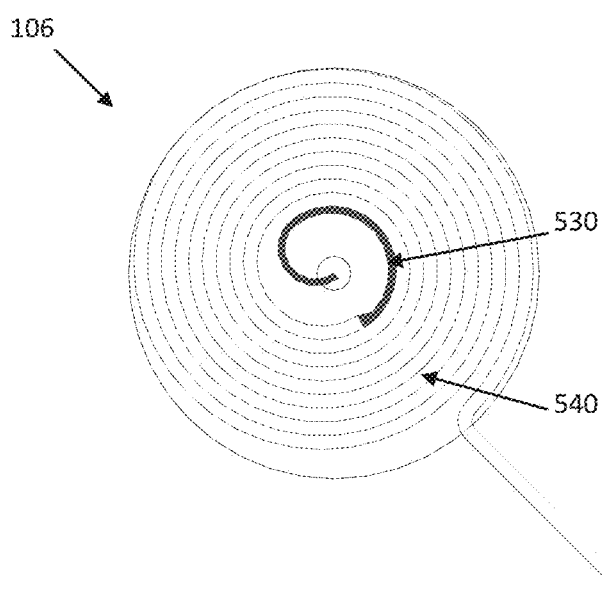
FIG. 5B depicts a microfluidic channel according to another embodiment shown and described herein.

Other embodiments for the microfluidic channel 106 are illustrated in FIGS. 5A and 5B. As shown in FIG. 5A; the microfluidic channel 106 has a composite geometry wherein the microfluidic channel cross-sectional dimensions at the highlighted end section are different compared to the cross-sectional dimensions of the rest of the microfluidic channel 106. The end microfluidic channel section 510 may have at least one dimension larger than the comparable dimension for the rest of the microfluidic channel 106. For example, the end microfluidic channel section 210 may be 300 µm wide×200 µm deep whereas the rest of the microfluidic channel 520 may be 200 µm wide×200 µm deep. As another example, the end microfluidic channel section 210 may be 300 µm wide×300 µm deep whereas the rest of the microfluidic channel 520 may be 200 µm wide×200 µm deep. This ensures that the end microfluidic channel section 210 has a lower flow resistance than the preceding channel. This is useful in ensuring optimum flow performance for the static incubation case. The embodiment shown in FIG. 5A may ensure that since the flow resistance for the front end of the liquid column (closer to outlet of the microfluidic channel 106) is lower than the flow resistance for the rear-end of the liquid column (at through-hole interface), the liquid will always retract backward from the outlet.

Another embodiment that can achieve is a similar effect is shown in FIG. 5B. In FIG. 5B, the initial microfluidic channel section 530 may be different compared to the cross-sectional dimensions of the rest of the microfluidic channel 540. The initial microfluidic channel section 530 may have at least one dimension smaller than the comparable dimension for the rest of the microfluidic channel 106. For example, the initial microfluidic channel section 530 may be 100 µm wide×200 µm deep whereas the rest of the microfluidic channel 106 may be 200 µm wide×200 µm deep. As another example, the initial microfluidic channel section 530 may be 100 µm wide×100 µm deep whereas the rest of the microfluidic channel 106 may be 200 µm wide× 200 µm deep. This ensures that the initial section has a higher flow resistance than the remainder. This will also ensure that the liquid always retract backward; i.e. away from the outlet rather than retracting into the microfluidic channel; i.e. away from the inlet. Furthermore, the use of a high resistance section at the start of the microfluidic channel is also advantageous for flow regulation for continuous-flow or flow-through mode.

Detection of Immunoassay Reactions Conducted within a Microfluidic Microplate

Hereinafter, methods for optimizing the detection of immunoassay reactions conducted within a microfluidic microplate 100 (e.g., the Optimiser™ microplates) are described. For example, the microfluidic microplate 100 may consist of the tapered loading well 104 connecting to the microfluidic channel 106 via the through hole 108 as shown in FIG. 2. The microfluidic channel 106 on the opposing face with respect to the loading well 104 may be designed to match the footprint/pitch of ANSI-SBS specifications for 96-well microplates.

The microfluidic microplate 100 may be used with chemi-fluorescence and chemiluminescence modes of detection. Between these two methods, the chemi-fluorescence method is more advantageous owing to the cumulative nature of the chemi-fluorescence substrate as opposed to the dynamic signal from a chemiluminescence substrate. The present disclosure focuses in particular on chemi-fluorescence based signal detection—typically for an immunoassay reaction—from microfluidic microplates, microfluidic strip well plates and microfluidic partial strip well plates.

For immunoassay reactions, a critical performance metric is the coefficient of variance (CV) of the assay signals. This is typically computed as either (a) CV of the raw optical signal acquired or (b) CV of the back calculated concentrations tested via the immunoassay methods (also referred to as assay CV). Of these computing methods, the latter is of greater significance and concern. Unless specifically described as signal CV, all descriptions of CV in the present disclosure describe the assay CV.

In a typical immunoassay reaction—a capture molecule is first added to the microfluidic microplate 100 and the capture molecule non-specifically adsorbs to the polystyrene surface of the microfluidic channels 106 (or microchannels). Note that commonly used methods such as covalent attachment of capture molecule are also possible. Then, the remaining sites are blocked by addition of an appropriate blocking buffer. When the block buffer is added to the loading well, the block buffer flushes out the capture molecule solution within the microfluidic channels 106 to the absorbent pad 112 at the distal end of the microfluidic channel 106 and the same process is repeated for subsequent liquids. Next, the sample containing the analyte of interest in added to the loading well. The capture (and detection) molecules are chosen to have high degree of specificity to the analyte of interest. As the sample is incubated within the microfluidic channel, the analyte of interest binds to the capture molecule. After addition of wash buffer (to remove unbound analyte), a detection molecule solution is added next. The detection molecules are typically labeled with either an enzyme label or a biotin label. If biotin labeled, streptavidin-enzyme conjugate is added as an additional solution after the detection molecule solution. After addition of wash buffer, to remove unbound detection molecules/ streptavidin-enzyme conjugate—a chemi-fluorescence substrate is added as the final solution. The enzyme label on the detection molecule (typically but not limited to HRP or AP) catalyzes the chemi-fluorescence substrate from a non-fluorescent to a fluorescent format. The chemi-fluorescence substrate continues to be catalyzed to the fluorescent format in the presence of HRP or AP enzyme labels until a saturation is reached where all the molecules of the substrate are converted to a fluorescent stage. As a result, the signal for a chemi-fluorescence reaction increases over time until it reaches eventual saturation.

Four methods of reading a microfluidic microplate are described with reference to FIGS. 6 through 10C.

Method 1: Read Time of a Microfluidic Microplate

Figure 6:
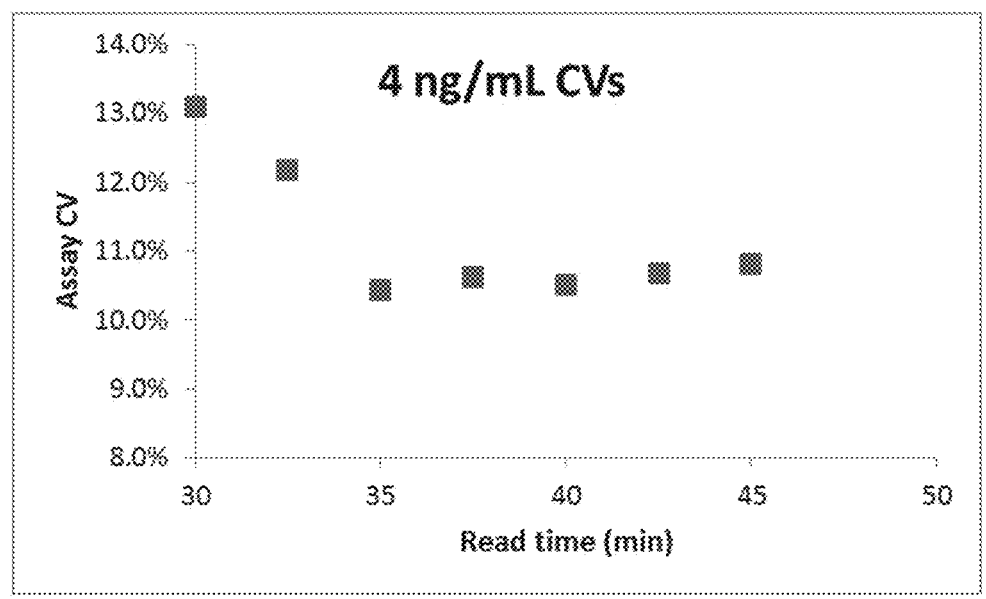
FIG. 6 depicts the effect of read time on assays CV's for a model Leptin assay according to one or more embodiments shown and described herein.

Unlike conventional microplates, where the detection substrate reaction with catalyzing enzyme is stopped by addition of (typically) an acid solution, the chemi-fluorescence reaction in a plurality of cells in the microfluidic microplate 100 is a continuous reaction. This is because mixing is very difficult to achieve in microfluidic channels and specifically in the microfluidic microplate (e.g., Optimiser™ design), addition of a liquid flushes the previous liquid out making use of a stop solution impossible. As a result, the reaction keeps developing the substrate until saturation. Owing to the differences in flow rates across 96 cells of the microfluidic microplate; the read time has a significant effect on assay performance. For instance, if substrate is added simultaneously to 2 adjacent wells (e.g., a first well 101 and a second well 103 as shown in FIG. 1) of the microfluidic microplate 100, a substrate may displace the wash buffer in the first well 101 and occupy the microfluidic channel 106 in, for example, 30 seconds. On the other hand, this same process may require, for example, 2 minutes in the second well 103. In this case, the substrate in the first well 101 will have a longer time to react with the enzyme label in the microfluidic channel 106 as compared to the second well 103 because the substrate in the first well 101 occupies the microfluidic channel 106 faster than the substrate in the second well 103 and is in ready for the reaction with the enzyme label earlier than the substrate in the second well 103. If the first well 101 and the second well 103 are tested with the same sample, the first well 101 will report a higher value than the second well 103 leading to increased CV. FIG. 6 shows the effect of read time on assays CV's for a model Leptin assay (test concentration 4 ng/mL; spiked in plasma).

The assay CV was computed by running 24 identical concentrations of 4 ng/mL Leptin spiked in plasma in 24 wells of the microfluidic microplate 100. A 7-pt standard curve with a blank where two-fold dilutions of known standard are used in the 7-pt calibration curve was used to calibrate the signal. The standard concentrations and the acquired signals were transformed to log 10 values. A log-log cubic fit standard curve was generated using the signals from the known standards. Signals from the 24 spiked wells were then used to calculate the concentration (based on the signal) using GraphPad Prism software. Unless otherwise noted, a similar method is used for all the results described in the present disclosure.

As shown in FIG. 6, the CVs initially drops rapidly and then slowly start rising. The initial drop is a result of the fact that longer times smooth the slight differences in flow rate (and hence the time it takes the substrate to fill the channel and start reacting with the HRP on the detection antibody). However, as the substrate reaches saturation the cells start exhibiting uneven signals with different cells reaching saturation at different times thus leading to increased CV's.

Note that assay CV is one of the key metrics. The other assay metric that is also affected by read time may be a recovery ratio. For high concentration samples, the higher HRP ratio bound to the sandwich leads to rapid development of the substrate whereas for lower concentration samples the signals develop at a slower rate. When the read times are extended, higher concentration samples reach saturation levels and depending on the range used for the standard curve can even exceed the top standard leading to poor recoveries. Read times within 30-35 min (from substrate addition) may be selected as read times for the microfluidic microplate 100.

Method 2: Use of a Compensating "Mask" to Account for Read Time Delays.

Figure 7:
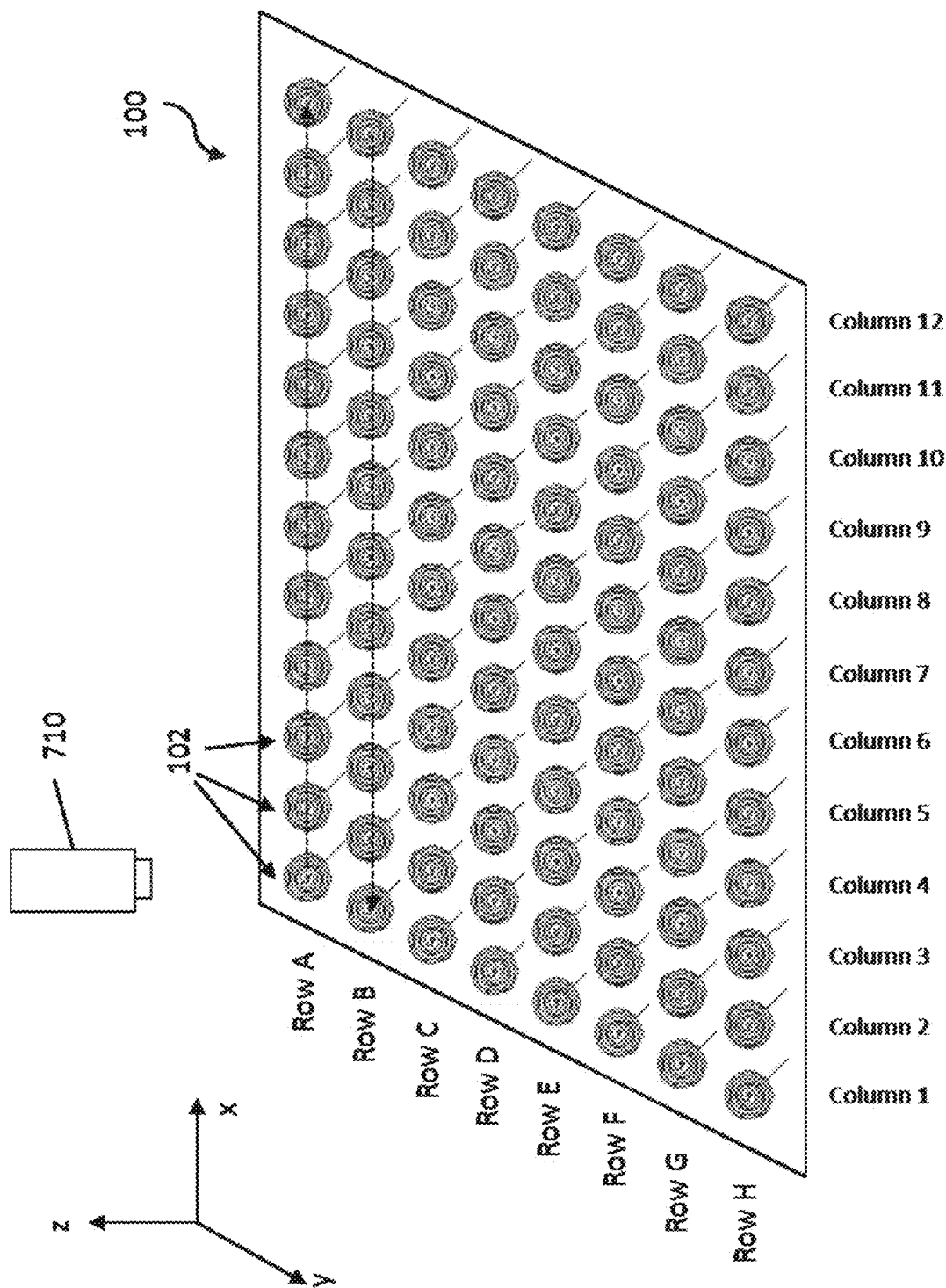
FIG. 7 depicts reading cells of the microfluidic microplate by a fluorescence reader according to one or more embodiments shown and described herein.

As noted above, the chemi-fluorescence reaction in cells 102 of the microfluidic microplate 100 progresses with increasing time. Most fluorescence readers are single probe readers—i.e. they read 1 well at a time—and a single read head scans the entire plate—typically in a snake-like pattern. FIG. 7 depicts a fluorescence reader 710 reading the cells 102 of the microfluidic microplate 100. The microfluidic microplate 100 extends along the +x axis direction (i.e., longitudinal direction) and the +y axis direction (i.e., lateral direction) as shown in FIG. 7. The fluorescence reader 710 is positioned above (i.e., +z direction) the microfluidic microplate 100.

As shown in FIG. 7, a fluorescence reader 710 reads the cells 102 in the order as indicated by arrows (i.e. read from well A1 to A12; then B12 to B1; C1 to C12; D12 to D1 and so forth). The read times for fluorescence reader 710 (e.g., a BioTek Flx800 and Tecan M200) to read a 96-well microplate are timed at about 51 seconds and 1:23 minute respectively. The read times may be in turn dependent on the number of "flashes" used to read a single well location. Typically, most fluorescence readers will read each well multiple times and the signals from these multiple reads are averaged to reduce any errors from the optical system of the reader (where each read is a "flash"). As one example, Tecan reader recommends using 25 flashes per well in fluorescence mode. If the number of flashes is increased or decreased, the total read time will increase or decrease accordingly. The durations listed above are based on the default settings for each manufacturer.

The interview of 51 seconds or 1:23 minute is a non-trivial (2.5% through 4%) fraction of the total read time (35 minutes). As a result, when a single concentration is tested across the entire plate, the signal from the lower rows (e.g. Rows G and H of the microfluidic microplate 100) is noticeably higher than the signal from the top rows (e.g., Rows A and B of the microfluidic microplate 100). This leads to increase in assay imprecision. To counter this effect, a compensation mask may be provided. The compensation mask divides raw signal values obtained from the cells to adjust for the delay in read times for the 96 individual cells of the microfluidic microplate 100. Three different concentrations of HRP (directly coated on a full plate) were read at different times and the rate of signal change was monitored for various concentrations at different times. A time based compensation mask was developed by averaging the rate of change at the various concentrations. As one example, the "reader mask" for the Tecan M200 for 30 minute reads is shown in Table 1 below.

TABLE 1

| Row | Column | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 1.0000 | 1.0009 | 1.0018 | 1.0027 | 1.0036 | 1.0046 | 1.0055 | 1.0064 | 1.0073 | 1.0082 | 1.0091 | 1.0100 |
| B | 1.0209 | 1.0200 | 1.0191 | 1.0182 | 1.0173 | 1.0164 | 1.0155 | 1.0146 | 1.0137 | 1.0127 | 1.0118 | 1.0109 |
| C | 1.0219 | 1.0228 | 1.0237 | 1.0246 | 1.0255 | 1.0264 | 1.0273 | 1.0282 | 1.0291 | 1.0301 | 1.0310 | 1.0319 |
| D | 1.0428 | 1.0419 | 1.0410 | 1.0401 | 1.0392 | 1.0382 | 1.0373 | 1.0364 | 1.0355 | 1.0346 | 1.0337 | 1.0328 |
| E | 1.0437 | 1.0446 | 1.0455 | 1.0464 | 1.0474 | 1.0483 | 1.0492 | 1.0501 | 1.0510 | 1.0519 | 1.0528 | 1.0537 |

TABLE 1-continued

| Row | Column | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| F | 1.0647 | 1.0637 | 1.0628 | 1.0619 | 1.0610 | 1.0601 | 1.0592 | 1.0583 | 1.0574 | 1.0565 | 1.0556 | 1.0546 |
| G | 1.0656 | 1.0665 | 1.0674 | 1.0683 | 1.0692 | 1.0701 | 1.0710 | 1.0719 | 1.0729 | 1.0738 | 1.0747 | 1.0756 |
| H | 1.0865 | 1.0856 | 1.0847 | 1.0838 | 1.0829 | 1.0820 | 1.0811 | 1.0801 | 1.0792 | 1.0783 | 1.0774 | 1.0765 |

The use of the read time delay compensation mask improves the assay precision and has been verified with multiple experiments as shown in Table 2 below. For each experiment shown in Table 2; 24 replicates of each listed concentration were tested on a plate (3 concentrations tested per plate) and the CV's are reported for singlet analysis.

TABLE 2

| Sample dilution | Leptin Conc. (ng/mL) | Assay CV w/o mask | Assay with mask |
|---|---|---|---|
| Neat | 2.1 | 12.5% | 11.0% |
| | 3.9 | 4.4% | 3.8% |
| | 96.0 | 18.4% | 9.5% |
| 2-fold | 4.0 | 8.3% | 7.3% |
| | 6.1 | 9.1% | 8.9% |
| | 100.0 | 65.6% | 13.6% |
| 4-fold | 6.17 | 13.9% | 11.9% |
| | 11.9 | 4.8% | 3.8% |
| | 28.3 | 5.7% | 4.7% |
| 20-fold | 39.2 | 8.8% | 7.8% |
| | 52.3 | 9.9% | 8.2% |
| | 93.6 | 15.2% | 14.2% |

Method 3: Offset Read Location

Figure 8A:
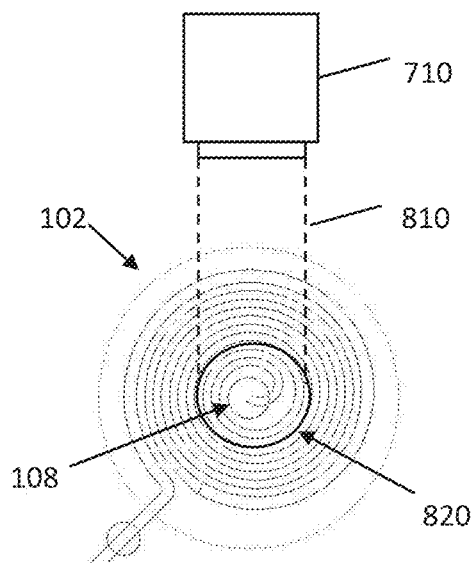
FIG. 8A depicts reading a cell of the microfluidic microplate by a fluorescence reader.

Most modern 96-well readers are also designed to read 384 well plates and in some cases 1536 well plates as well. In order to achieve this, the beam diameter for the excitation beam (for fluorescence mode) is about 3 millimeter diameter (or smaller if the reader is also designed to read 1536 well plates) and is usually centered for 96 wells. For example, as shown in FIG. 8A, the fluorescence reader 710 emits excitation beam 810 having about 3 millimeter diameter to an area 820 on the cell 102. The area 820 may be a circled area co-centered with the cell 102 and having a diameter of about 3 millimeter or less.

The manufacturing process for microfluidic microplates involves a proprietary surface treatment step for the loading well. We hypothesize that the surface treatment could affect the inlet portion of the microfluidic channels in some cases and affect the hydrophobic binding mechanism for the capture molecule. This could to slight changes in signal from the affected cells when compared to adjacent unaffected cells leading to inaccuracy and increased imprecision.

Figure 8B:
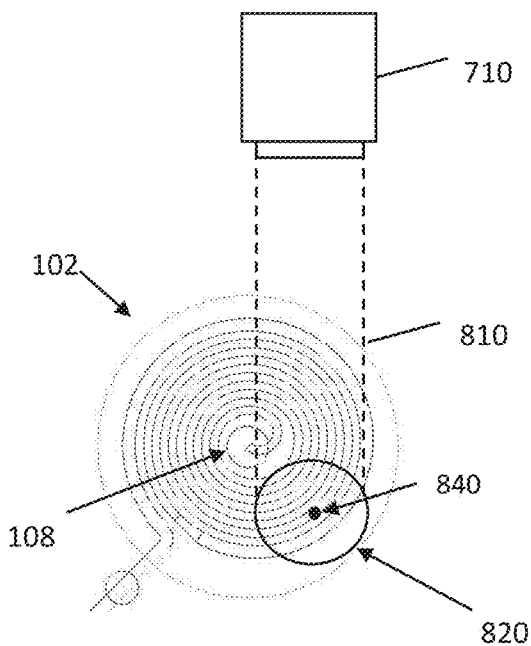
FIG. 8B depicts reading a cell of the microfluidic microplate by a fluorescence reader according to one or more embodiments shown and described herein.

FIG. 8B depicts the fluorescence reader 710 emitting excitation beams according to one or more embodiments of the present disclosure. FIG. 8B depicts a partial view of the microfluidic microplate 100 in FIG. 7. In embodiments, the fluorescence reader 710 emits excitation beam 810 to an area 830. The area 830 may be a circled area focusing on a target location 840, and the target location 840 is deviated from the center of the cell 102. The area 830 may not overlap with the through hole 108 of the cell 102. For example, the target location 840 may be more than 1.5 millimeters away from the center of the cell 102. As shown in FIG. 8B, if the cell 102 is read at an offset such that the read window corresponding to the area 830 does not include the through hole 108 the variance due to inconsistent behaviors at the through hole 108 can be avoided and thus, leading to improved precision. In embodiments, the target location 840 may be located about 1.5 millimeters from the center of the cell 102 in a direction rotated clockwise by 45 degrees from the +x axis direction.

Multiple offset positions were tested to evaluate this effect and the offset position shown in FIG. 8B was selected as one of the optimal positions. Table 3 shows the results for 3 experiments (2-fold dilution) for Leptin assay precision where the plates were read with the conventional (centered) and new offset read locations. A significant and consistent improvement is noted in assay CV for all cases. The offset read window is located such that the center of the read window is located 1.5 millimeters away from the center of the through hole 108 at a −45 degree angle from the +x axis direction.

TABLE 3

| | Leptin Con. (ng/mL) | | |
|---|---|---|---|
| Read location | 5 | 45 | 100 |
| center | 8.6% | 5.5% | 10.9% |
| offset | 4.8% | 5.0% | 4.8% |
| center | 7.3% | 12.8% | 3.9% |
| offset | 4.3% | 4.0% | 6.5% |
| center | 5.0% | 4.2% | 9.4% |
| offset | 3.6% | 3.1% | 5.3% |

The method for identifying the optimal read windows is as follows: the microfluidic microplate 100 is imaged using a Typhoon 8600 scanner (e.g., Amersham). Fully developed chemi-fluorescence substrate was prepared by mixing a small volume of 2 ug/mL HRP with the substrate solution. The substrate develops to full signal in about 2 minutes. Then, the substrate was diluted at varying concentrations to determine 2 dilutions that yielded a strong signal with the Typhoon scanner. The microfluidic microplate 100 was read with a scan setting of 50 micrometers, 100 micrometers, and 200 micrometers. The 200 micrometers scan provides a very coarse image and was rejected. The 50 micrometers scan provides the best quality image but the imaging time per plate (about 28 minutes) is too long to be practically useful. As a practical compromise 100 micrometer scan setting was used. Scanning the entire plate at 100 micrometers setting yields 1,400×1,000=1.4 million data points per plate. Images were analyzed using the Image J software (NIH) and the analyzed results were exported as data tables to MS Excel.

Figure 9:
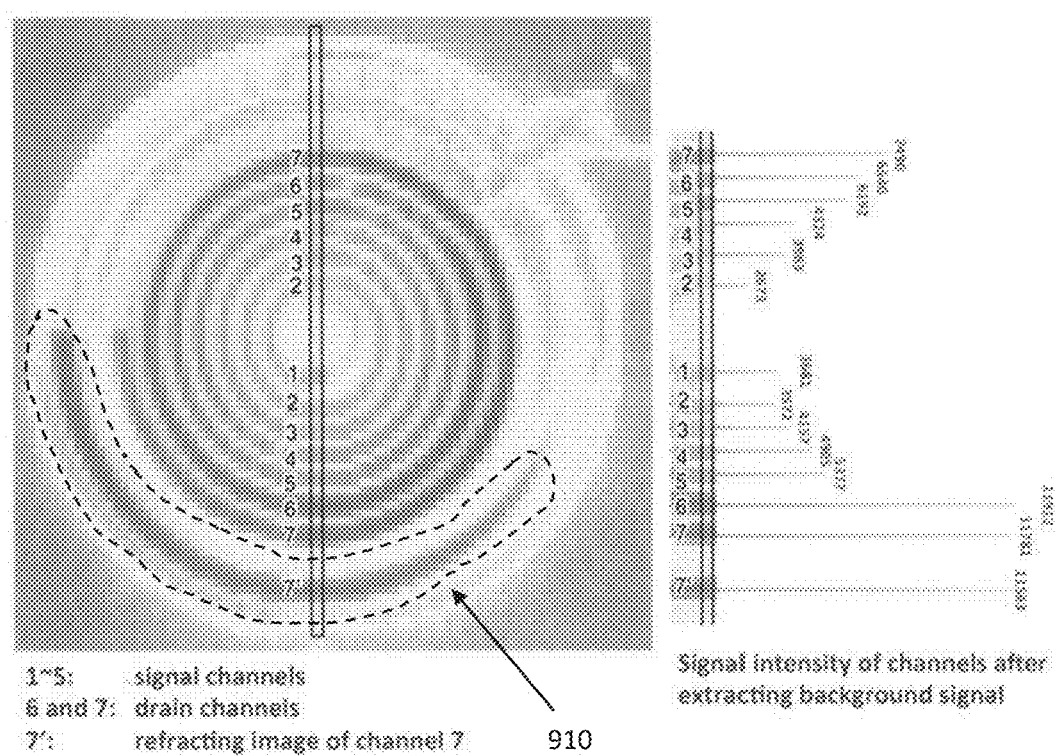
FIG. 9 depicts an image of signals read from a cell of the microfluidic microplate according to one or more embodiments shown and described herein.

A closer analysis of an individual cell shows some interesting trends. As shown in FIG. 9, the signal is concentrated in the spiral microfluidic channels as expected. In embodiments, the microfluidic channel 106 may include two different channel widths—a narrower section near the inlet and a wider section near the outlet, for example, as shown in FIG. 5A. In embodiments, the channel 1 through channel 5 in FIG. 9 are signal channels having a narrower section (e.g., 200 μm wide×200 μm deep), and the channel 6 through channel 7 in FIG. 9 are drain channels having a wider section (e.g., 300 μm wide×300 μm deep). A cross-sectional sweep of the signal shows that the larger area/volume wider channels contribute a significant percentage of the overall signal. Also, due to the sloping well design—an optical artifact 910 (i.e., refracting image of channel 7) is created and reading this would lead to spuriously high signals. Note that the orientation of the cell 102 shown in FIG. 9 is a mirror image of the actual orientation of the cells as shown in FIG. 8B. Note also that read windows with lower variance (than center reads) were identified by analysis of raw signal variance.

Figure 10A:
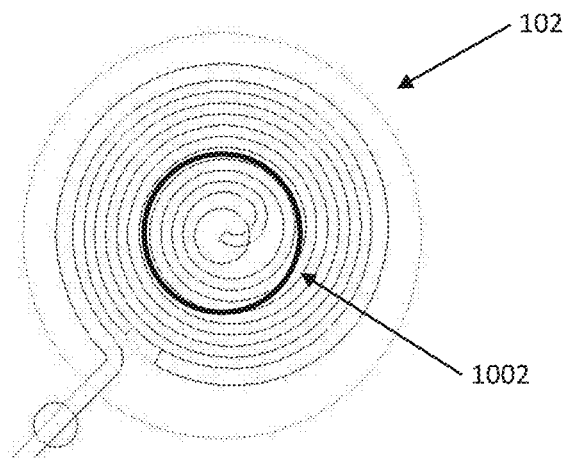
FIG. 10A depicts reading a cell of the microfluidic microplate based on settings for a 96 well plate.
Figure 10B:
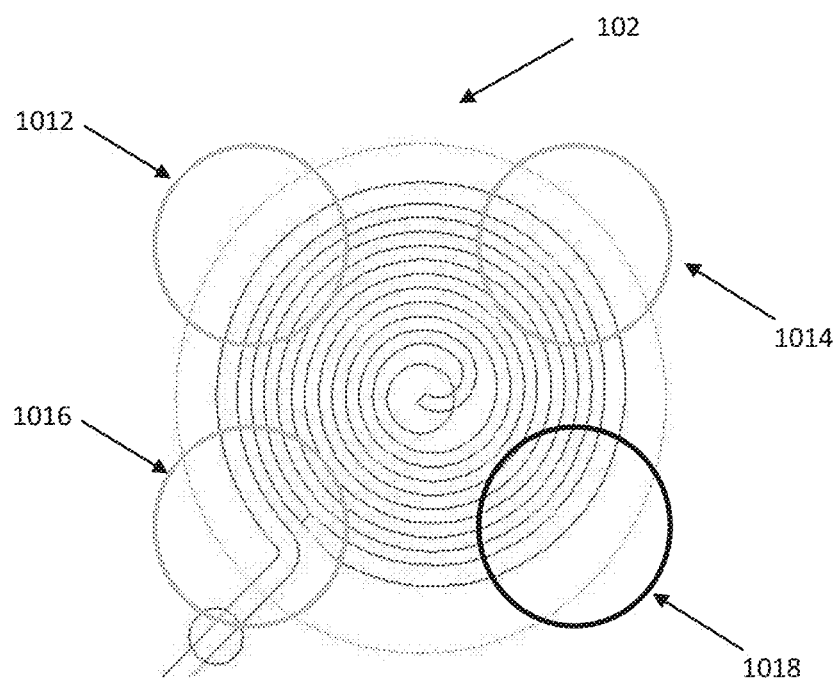
FIG. 10B depicts reading a cell of the microfluidic microplate based on settings for a 384 well plate.
Figure 10C:
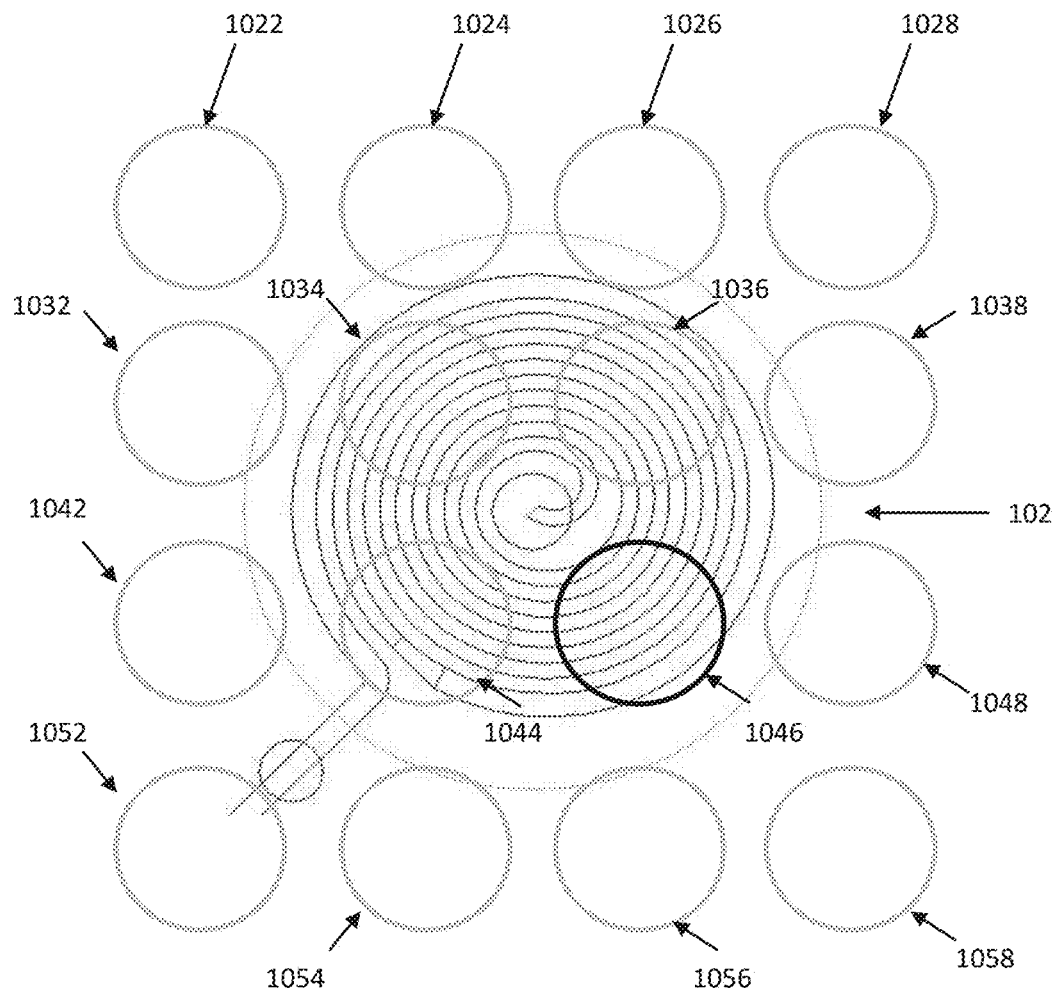
FIG. 10C depicts reading a cell of the microfluidic microplate based on settings for a 1536 well plate.

The operation of readers allows for 2 different methods to achieve the offset reads. One option is to configure the fluorescence reader 710 to read the microfluidic microplate with the settings for a 384 (or 1536) well plate. This is illustrated in FIGS. 10A, 10B, and 10C. As shown in FIGS. 10A, 10B, and 10C, by changing the plate definition from 96 to 384 or 1536 well plate automatically changes the read location. FIG. 10A depicts reading the cell 102 of the microfluidic microplate 100 based on settings for a 96 well plate. In FIG. 10A, one area 1002 may be read with respect to the single cell 102. FIG. 10B depicts reading the cell 102 of the microfluidic microplate 100 based on settings for a 384 well plate. In FIG. 10B, four different areas 1012, 1014, 1016, and 1018 may be read with respect to the single cell 102. FIG. 10C depicts reading the cell 102 of the microfluidic microplate 100 based on settings for a 1536 well plate. In FIG. 10C, sixteen different areas 1022, 1024, 1026, 1028, 1032, 1034, 1036, 1038, 1042, 1044, 1046, 1048, 1052, 1054, 1056, and 1058 may be read with respect to the single cell 102.

For instance, one can program the fluorescence reader 710 to read the microfluidic microplate 100 as a 384-well plate where all 384 "wells" are read. Alternately, it is also possible to program the fluorescence reader 710 where only the bottom-right area 1018 in a 4-cell group is read as shown in FIG. 10B. The latter approach (reading selected wells in a higher density configuration) is preferred since it reduces the overall read time (and potential variance as outlined in Method 2 previously).

Another method is to introduce the offset by changing the well definition of the microfluidic microplate itself for the reading operation. The ANSI-SBS specifications define certain key parameters for 96-well plates—for instance that the well-to-well spacing must be 9 mm in both the horizontal and vertical orientations. However, manufacturers have the flexibility of selecting other parameters of the plate design—such as whether the plate has an identifying 45 degree taper at the A1 well location. As a result, all fluorescence readers allow users to create a "plate definition" wherein key parameters of the plate are defined. This allows the reader to precisely position the reader head at the desired location for reading the plates. One set of these definition parameters include the position of the top-left cell (e.g., the cell 102 on Row A and Column 1 in FIG. 7) and the position of the bottom-right cell (e.g., the cell on Row H and Column 12 in FIG. 7) with respect to the edges of the microfluidic microplate 100.

Table 4 below shows the actual locations of these 2 wells for the microfluidic microplate as well as the offset locations to shift the read location to the area shown in FIG. 7. As seen from the changes in the "actual" versus "offset" locations for the top left cell, a higher value of Y is defined (read location is thus lower than center since 0 on the Y-axis is the top edge of the plate) and a higher value of X is defined (read location is thus to the right of the center since 0 on the X-axis is the left edge of the plate for top left well).

TABLE 4

|  |  | Y (micron) | X (micron) |
|---|---|---|---|
| Actual | Center of top left cell from top left edge | 11240 | 14380 |
|  | Center of bottom right cell from top left edge | 74240 | 113380 |
| Offset | Center of top left cell from top left edge | 12300 | 15440 |
|  | Center of bottom right cell from top left edge | 75200 | 114440 |

Method 4: Use of Multiple Offset Read Locations

Multiple areas (or read windows) that exhibit lower variance than areas co-centered with the cells 102 of the microfluidic microplate 100 may be identified. This was confirmed by reading the plates with the identified offsets when actual immunoassays were performed for Leptin containing samples in Optimiser™ plates and the selected preferred read windows are described below:

N1.5: location where the center of the read window is located 1.5 millimeters away from the center of the cell of the microfluidic microplate along a +90 degree angle (North direction) from the +x axis direction in FIG. 8B.

S1.5: location where the center of the read window is located 1.5 millimeters away from the center of the cell of the microfluidic microplate along a −90 degree angle (South direction) from the +x axis direction in FIG. 8B.

SE45: location where the center of the read window is located 1.5 millimeters away from the center of the cell of the microfluidic microplate along a −45 degree angle (Southeast direction) from the +x axis direction in FIG. 8B.

NE45: location where the center of the read window is located 1.5 millimeters away from the center of the cell of the microfluidic microplate along a +45 degree angle (Northeast direction) from the +x axis direction in FIG. 8B.

The offset locations; together with the actual locations for the top-left and bottom-right wells used for plate definition for reader plate definition are disclosed in Table 5 below.

TABLE 5

|  |  | Y | X |
|---|---|---|---|
| 96 well | Top L | 11240 | 14380 |
|  | Bottom R | 74240 | 113380 |
| N1.5 | Top L | 9740 | 14380 |
|  | Bottom R | 72740 | 113380 |
| S1.5 | Top L | 12740 | 14380 |
|  | Bottom R | 75740 | 113380 |
| SE45 | Top L | 12300 | 15440 |
|  | Bottom R | 75300 | 114440 |
| NE45 | Top L | 10180 | 15440 |
|  | Bottom R | 73180 | 114440 |

Multiple plate definitions were created for reading the microfluidic microplates at the specified offset location. Following the completion of the immunoassay protocol, each Optimiser™ plate was read multiple times using the specified offset read definitions—i.e. the plate was read using the N1.5 definition, NE45 definition, SE45 definition, and S1.5 definition. The other parameters that are used for the plate definition include: Number of rows=8; Number of columns=12; Plate width=85480 microns; Plate length=127760 microns; Plate height=14350 microns; Well diameter=6000 microns.

Of the multiple offset read locations; the SE45 location yields low variance signals on the most consistent basis as a single offset read location. However, the use of multiple offset locations yields even more consistent results with respect to reduced assay CVs. Illustrative results for a Leptin assay tested using this method are shown in Table 6 below. Table 6 shows effect of using multiple offset read locations and averaging or using median of calculated concentrations from each offset read locations on the assay CV. All values are the % CV for a Leptin assay tested at 3 different concentration levels as listed.

TABLE 6

|  | S1.5 | SE45 | NE45 | N1.5 | Average | Median |
|---|---|---|---|---|---|---|
| Low (5 ng/mL) | 5.1% | 5.5% | 4.6% | 5.1% | 4.7% | 4.8% |
| Mid (45 ng/mL) | 4.3% | 4.1% | 5.1% | 3.9% | 3.9% | 3.9% |
| High (90 ng/mL) | 5.4% | 6.2% | 8.3% | 7.2% | 5.9% | 5.9% |

Table 6 shows the computed assay CV for each individual offset read location at 3 different concentrations. Table 6 also shows the assay CV results when the calculated concentrations from each offset read location are averaged and then the CV of the averaged values is computed. For instance, well A4 is read using the S1.5, SE45, NE45, and N1.5 offsets. Then the method described previously is used to calculate the unknown concentration based on each offset reading method. The 4 calculated concentrations are then averaged. The averaged calculated concentrations from 24 wells are then used to compute the assay CV for a given concentration. Table 6 also shows the assay CV results when the median of the calculated concentration from the 4 different offset read locations is used instead of averaging the calculated concentrations from the 4 different offset read locations.

Table 6 shows some interesting facts. For low concentration samples, the least variance is observed for NE45 read location. For mid concentration samples, the least variance is observed for the SE45 location. For high concentration samples, the least variance is observed for the S1.5 read location. For all 3 concentrations, the averaging method yields variance in between the lowest and highest variances of the 4 offset reads. For all 3 concentrations, the median method yields variance in between the lowest and highest variances of the 4 offset reads.

As described previously, over multiple experiments; the SE45 offset read location shows the highest instance of low CV compared to the other 3 offset read locations. However, this is not always the case as shown in Table 6. On the other hand using the averaging or median method; always results in assay CV equal to or greater than the offset read location that shows lowest CV and also where the assay CV is always less than the offset read location that shows the highest CV. Accordingly, the use of the averaging or median method is preferred over the use of any one single offset read location.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed:

1. A method for reading a microfluidic microplate having a plurality of cells, the method comprising:
    determining target locations on the microfluidic microplate, each of the target locations being deviated from a center of each of the cells; and
    directing a beam centered at each of the target locations perpendicular to the microfluidic microplate, the beam having a predetermined diameter,
    wherein each of the plurality of cells comprising:
        a well structure including a side wall for a loading well;
        a through hole at a center of a base of the well structure; and
        a microfluidic channel formed in a spiral pattern configured to start from a first end of the microfluidic channel and end with a second end of the microfluidic channel at the base of the well structure, wherein the first end of the microfluidic channel is connected to the through hole, and the second end of the microfluidic channel includes an outlet hole.

2. The method of claim 1, wherein each of the target locations is located about 1.5 millimeters apart from the center of each of the cells.

3. The method of claim 1, wherein the microfluidic microplate is extended in a longitudinal direction and a lateral direction, and
    each of the target locations is located about 1.5 millimeters apart from the center of each of the cells in a direction rotated clockwise by 45 degrees from the longitudinal direction.

4. The method of claim 1, wherein the microfluidic microplate is extended in a longitudinal direction and a lateral direction, and
    each of the target locations is located about 1.5 millimeters apart from the center of each of the cells in the lateral direction.

5. The method of claim 1, wherein the microfluidic microplate is extended in a longitudinal direction and a lateral direction, and
    each of the target locations is located about 1.5 millimeters apart from the center of each of the cells in an opposite direction to the lateral direction.

6. The method of claim 1, wherein the microfluidic microplate is extended in a longitudinal direction and a lateral direction, and
    each of the target locations is located about 1.5 millimeters apart from the center of each of the cells in a direction rotated counterclockwise by 45 degrees from the longitudinal direction.

7. The method of claim 1, wherein the predetermined diameter is about 3 millimeters.

8. The method of claim 1, wherein an area directed by the beam on the microfluidic microplate does not overlap with the through hall.

9. The method of claim 1, wherein dimensions of the microfluidic microplate conform to ANSI standards.

10. The method of claim 1, wherein the microfluidic channel includes a first section close to the first end and a second section close to the second end, and a width of the first section is narrower than a width of the second section.

11. A method for reading a microfluidic microplate having a plurality of cells, the method comprising:
- determining a plurality of reading locations for each of the plurality of cells, each of the reading locations being deviated from a center of each of the plurality of cells; and
- directing a beam centered at each of the plurality of reading locations perpendicular to the microfluidic microplate, the beam having a predetermined diameter;
- wherein each of the plurality of cells comprising:
  - a well structure including a side wall for a loading well;
  - a through hole at a center of a base of the well structure; and
  - a microfluidic channel formed in a spiral pattern configured to start from a first end of the microfluidic channel and end with a second end of the microfluidic channel at the base of the well structure, wherein the first end of the microfluidic channel is connected to the through hole, and the second end of the microfluidic channel includes an outlet hole.

12. The method of claim 11, wherein the plurality of reading locations include locations that are located about 1.5 millimeters apart from the center of each of the cells.

13. The method of claim 11, wherein the microfluidic microplate is extended in a longitudinal direction and a lateral direction, and
- wherein the plurality of reading locations include at least one of a location located about 1.5 millimeters apart from the center of each of the cells in a direction rotated clockwise by 45 degrees from the longitudinal direction, a location located about 1.5 millimeters apart from the center of each of the cells in the lateral direction, a location located about 1.5 millimeters apart from the center of each of the cells in an opposite direction to the lateral direction, and a location located about 1.5 millimeters apart from the center of each of the cells in a direction rotated counterclockwise by 45 degrees from the longitudinal direction.

14. The method of claim 11, wherein an area directed by the beam on the microfluidic microplate does not overlap with the through hall.

15. The method of claim 11, wherein dimensions of the microfluidic microplate conform to ANSI standards.

16. The method of claim 11, wherein the microfluidic channel includes a first section close to the first end and a second section close to the second end, and a width of the first section is narrower than a width of the second section.

17. A method for reading a microfluidic microplate having a plurality of cells, the method comprising:
- directing a beam at each of the plurality of cells perpendicular to the microfluidic microplate;
- obtaining assay signals for each of the plurality of cells; and
- compensating the assay signals based on timings of reading the plurality of cells,
- wherein each of the plurality of cells comprising:
  - a well structure including a side wall for a loading well;
  - a through hole at a center of a base of the well structure; and
  - a microfluidic channel formed in a spiral pattern configured to start from a first end of the microfluidic channel and end with a second end of the microfluidic channel at the base of the well structure, wherein the first end of the microfluidic channel is connected to the through hole, and the second end of the microfluidic channel includes an outlet hole.

18. The method of claim 17, further comprising:
- determining target locations on the microfluidic microplate, each of the target locations deviated from a center of each of the cells; and
- directing the beam centered at each of the target locations perpendicular to the microfluidic microplate, the beam having a predetermined diameter.

19. The method of claim 17, wherein the microfluidic microplate includes 96 wells.

20. The method of claim 17, wherein the microfluidic channel includes a first section close to the first end and a second section close to the second end, and a width of the first section is narrower than a width of the second section.

* * * * *